United States Patent [19]

Sick et al.

[11] Patent Number: 4,996,155

[45] Date of Patent: Feb. 26, 1991

[54] BACILLUS THURINGIENSIS GENE ENCODING A COLEOPTERAN-ACTIVE TOXIN

[75] Inventors: August J. Sick; Thomas E. Gilroy, both of San Diego, Calif.

[73] Assignee: Mycogen Corporation, San Diego, Calif.

[21] Appl. No.: 164,044

[22] Filed: Mar. 4, 1988

[51] Int. Cl.$^5$ ................... A01N 63/00; C12N 1/13; C12N 1/15; C12N 1/21
[52] U.S. Cl. .................. 435/252.3; 435/69.1; 435/711; 435/91; 435/172.1; 435/172.3; 435/252.2; 435/254; 435/257; 435/320.1; 435/822; 435/911; 435/946; 536/27; 424/93; 935/6; 935/9; 935/22; 935/59; 935/60; 935/64; 935/66; 935/68
[58] Field of Search ................ 435/68, 70, 69.1, 71.1, 435/91, 172.1, 172.3, 252.3, 252.31, 252.32, 252.33, 252.34, 252.35, 252.5, 254, 257, 320, 822, 911, 946; 536/27; 935/6, 9, 22, 59, 60, 64, 66, 68, 72, 73, 74, 75

[56] References Cited

U.S. PATENT DOCUMENTS 4,448,885 5/1984 Schnepf et al. .
4,467,036 8/1984 Schnepf et al. .
4,771,131 9/1988 Herrnstadt et al. .................. 536/27

OTHER PUBLICATIONS

Thorne et al. 1986, *J. Bacteriol.* 166(3): 801–811.
Schnepf, H. E. and Whitely, H. R. (1981) "Cloning and Expression of the *Bacillus Thuringiensis* Crystal Protein Gene in *Escherichia coli*," Proc. Natl. Acad. Sci. USA 78:2893–2897.

*Primary Examiner*—Richard A. Schwartz
*Assistant Examiner*—Richard C. Peet
*Attorney, Agent, or Firm*—Saliwanchik & Saliwanchik

[57] ABSTRACT

A novel *B.t.* toxin gene encoding a protein toxic to coleopteran insects has been cloned from a novel coleopteran-active *B. thuringiensis* microbe. The DNA encoding the *B.t.* toxin can be used to transform various prokaryotic and eukaryotic microbes to express the *B.t.* toxin. These recombinant microbes can be used to control coleopteran insects in various environments.

23 Claims, 9 Drawing Sheets

FIG.1-1

```
                                              Met
         10         20         30    ↓      40         50         60
  1 ATGATAAGAA TGGGAGGAAG AAAAATGAAT CCAAACAATC GAAGTGAATA TGATACGATA
 61 AAGGTTACAC CTAACAGTGA ATTGCCAACT AACCATAAAT AATATCCTTT AGCTGACAAT
121 CCAAATTCGA CACTAGAAGA ATTAAATTAT AAAGAATTTT TAAGAATGAC TGCAGACAAT
181 TCTACGGAAG TGCTAGACAG CTCTACAGTA AAAGATGCAG TTGGGACAGG AATTTCTGTT
241 GTAGGACAGA TTTTAGGTGT TGTAGGGGTT CCATTTGCTG GGGCGCTCAC TTCATTTTAT 310        320        330        340        350        360
301 CAATCATTTC TTAACGCTAT ATGGCCAAGT GATGCTGACC CATGGAAGGC TTTTATGGCA
361 CAAGTGGAAG TACTGATAGA TAAGAAAATA GAGGAGTATG CTAAAAGTAA AGCTCCTGCA
421 GAGTTACAGG GTCTTCAAAA TAATTTTGAA GATTATGTAA ATGCGTTGGA TTCCTGGAAG
481 AAAGCGCCTG TAAATTTACG AAGTCGAAGA AGCCAAGATC GAATAAGAGA ACTTTTTCT
541 CAAGCAGAAA GCCATTTTCG TAATTCCATG CCGTCATTTG CGGTTTCCAA ATTCGAAGTT 610        620        630        640        650        660
601 CTGTTTCTAC CAACATATGC ACAAGCTGCA AATACACATT TATTGCTATT AAAAGATGCT
661 CAAGTTTTTG GAGAAGAATG GGGATATTCT TCAGAAGATA TTGCTGAATT TTATCAAAGA
721 CAATAAAAAC TTACGCAACA ATACACTGAC CATTGTGTCA ATTGGTATAA TGTTGGATTA
781 AATAGTTTAA GAGGTTCAAC ATATGATGCA TTAACCGTTT TTAACCGTTT TCGCAGAGAA
841 ATGACATTAA CTGTATTAGA TCTAATTGTA TTATTCCCAT TTTATGATGT TCGGTTATAC
```

FIG.1-2

```
        910        920        930        940        950        960
 901 TCAAAAGGAG TTAAAACAGA ACTAACAAGA GACATTTTTA CAGATCCAAT TTTTACACTC
 961 AATGCTCTTC AAGAGTATGG ACCAACTTTT TCGAGTATAG AAAACTCTAT TCGAAAACCT
1021 CATTATTTG ATTATTGCG TGGGATTGAA TTTCATACGC GTCTTCGACC TGGTTACTCT
1081 GGGAAAGATT CTTTCAATTA TTGGTCTGGT AATTATGTAG AAACTAGACC TAGTATAGA
1141 TCTAATGATA CAATCACTTC CCCATTTTAT GGAGATAAAT CTATTGAACC TATACAAAAG 1210       1220       1230       1240       1250       1260
1201 CTAAGCTTTG ATGGACAAAA AGTTTATCGA ACTATAGCTA ATACAGACAT AGCGGCTTTT
1261 CCGGATGGCA AGATATATTT TGGTGTTACG AAAGTTGATT TTAGTCAATA TGATGATCAA
1321 AAAAATGAAA CTAGTACACA AACATATGAT TCAAAAGAT ACAATGGCTA TTTAGTGCA
1381 CAGGATTCTA TCGACCAATT ACCACCAGAA ACAACAGATG AACCACTTGA AAAAGCATAT
1441 AGTCATCAGC TTAATTACG AGAATGTTTC TTAATGCAGG ACCGTCGTGG AACAATTCCA 1510       1520       1530       1540       1550       1560
1501 TTTTTACTT GGACACATAG AAGTGTAGAC TTTTTAATA CAATTGATGC TGAAAAAATT
1561 ACTCAACTTC CAGTAGTGAA AGCATATGCC TTGTCTTCAG GCGCTTCCAT TATTGAAGGT
1621 CCAGATTCA CAGGAGGAA TTTACTATTC CTAAAGAAT CTAGTAATTC AATTGCTAAA
1681 TTTAAAGTTA CCTTAAATTC AGCAGCCTTG TTACAACGAT ATCGCGTAAG AATACGCTAT
1741 GCTTCAACCA CTAACCTACG ACTTTTCGTG CAAAATTCAA ACAATGATTT TCTTGTCATC 1810       1820       1830       1840       1850       1860
1801 TACATTAATA AAACTATGAA TATAGATGGT GATTAACAT ATCAAACATT TGATTTCGCA
1861 ACTAGTAATT CTAATATGGG ATTCTCTGT GATACAAATG ACTTTATAAT AGGAGCAGAA
1921 TCTTTCGTTT CTAATGAAAA AATCTATATA GATAAGATAG AATTTATCCC AGTACAA
```

FIG.2-1

```
                                                5                  10                 15
  1  Met Asn Pro Asn Arg Ser Glu Tyr Asp Thr Ile Lys Val Thr
 16  Pro Asn Ser Leu Pro Thr Asn His Asn Gln Tyr Pro Leu Ala
 31  Asp Asn Pro Asn Ser Thr Leu Glu Leu Asn Tyr Lys Glu Phe
 46  Leu Arg Met Thr Ala Asp Asn Ser Thr Glu Val Leu Asp Ser Ser
 61  Thr Val Lys Asp Ala Val Gly Thr Gly Ile Ser Val Val Gly Gln
 76  Ile Leu Gly Val Val Gly Val Pro Phe Ala Gly Ala Leu Thr Ser
 91  Phe Tyr Gln Ser Phe Leu Asn Thr Ile Trp Pro Ser Asp Ala Asp
106  Pro Trp Lys Ala Phe Met Ala Gln Val Glu Val Leu Ile Asp Lys
121  Lys Ile Glu Glu Tyr Ala Lys Ser Lys Ala Leu Ala Glu Leu Gln
136  Gly Leu Gln Asn Asn Phe Glu Asp Tyr Val Asn Ala Leu Asn Ser
151  Trp Lys Lys Ala Pro Val Ser Leu Arg Ser Arg Arg Ser Gln Asp
166  Arg Ile Arg Glu Leu Phe Ser Gln Ala Leu Asn Leu Ser Gln Asn Asp
181  Ser Met Pro Ser Phe Ala Val Ser Lys Phe Glu Val His Phe Arg Asn
196  Pro Thr Tyr Ala Gln Ala Ala Asn Thr His Leu Phe Leu Leu Phe Leu
211  Asp Ala Gln Val Phe Gly Glu Glu Trp Gly Tyr Ser Ser Glu Asp Lys
226  Ile Ala Glu Phe Tyr Gln Arg Gln Leu Lys Leu Thr Gln Gln Tyr Asp
241  Thr Asp His Cys Val Asn Tyr Trp Ala Trp Val Gly Leu Asn Ser Leu
256  Arg Gly Ser Thr Tyr Ala Asp Leu Val Lys Phe Asn Arg Phe Arg Arg
271  Arg Glu Met Thr Leu Thr Val Leu Asp Leu Ile Val Leu Phe Pro
286  Phe Tyr Asp Val Arg Leu Tyr Ser Lys Gly Val Lys Thr Glu Leu
301  Thr Arg Asp Ile Phe Thr Asp Pro Ile Phe Thr Leu Asn Ala Leu
```

FIG.2-2

```
                                  5                   10                  15
316  Gln Glu Tyr Gly Pro Thr Phe Ser Ser Ile Glu Asn Ser Ile Arg
331  Lys Pro His Leu Phe Asp Tyr Leu Arg Gly Ile Glu Phe His Thr
346  Arg Leu Arg Pro Gly Tyr Ser Lys Asp Gly Ser Phe Asn Tyr Trp
361  Ser Gly Asn Tyr Val Glu Tyr Arg Pro Ser Ile Gly Ser Asn Asp
376  Thr Ile Thr Ser Pro Phe Gly Tyr Ser Lys Val Tyr Arg Pro Ile
391  Gln Lys Leu Pro Phe Asp Gly Gln Lys Val Tyr Arg Thr Ile Ala
406  Asn Thr Asp Ile Ala Ala Phe Pro Asp Gly Ile Lys Tyr Phe Gly
421  Val Thr Lys Val Asp Phe Ser Gln Tyr Asp Lys Gln Asn Asn Glu
436  Thr Ser Gln Thr Phe Ser Tyr Asn Lys Arg Tyr Asn Gly Tyr Leu
451  Gly Ala Asp Ser Ile Thr Asp Lys Asn Arg Leu Pro Glu Thr Asp
466  Glu Pro Leu Glu Pro Leu Asp Leu Pro Leu Asn Pro Glu Thr Glu
481  Cys Phe Leu Gln Asp Arg Arg Ile Ser Gln Thr Ile Pro Phe Thr
496  Trp His Arg Ser Val Asp Phe Lys Asn Thr Ile Asp Ala Ala Glu
511  Lys Ile Thr Arg Leu Pro Val Val Lys Ala Tyr Ala Leu Ser Ser
526  Gly Ala Ser Ile Ile Glu Gly Pro Gly Phe Thr Gly Gly Asn Leu
541  Leu Phe Leu Lys Ser Asn Ser Ile Lys Ala Lys Phe Val Lys Val
556  Thr Leu Asn Ser Ala Leu Gln Leu Arg Tyr Arg Val Arg Ile Arg
571  Arg Tyr Ala Thr Thr Asn Leu Arg Ile Phe Leu Phe Val Gln Asn Ser
586  Asn Asn Asp Phe Thr Val Ile Tyr Ile Asn Lys Thr Met Asn Ile
601  Asp Gly Asp Leu Tyr Thr Gln Thr Phe Thr Phe Asp Phe Ala Ser
616  Ser Asn Met Gly Leu Phe Tyr Ser Gly Asp Thr Asn Asp Ala Thr Asn
631  Ala Glu Ser Phe Gly Val Phe Ser Ser Asn Lys Ile Ile Asp Gly
646  Glu Phe Ile Pro Val Gln Lys Ile Ile
```

FIG.3-1

| | | | | | 5 | | | | | 10 | | | | | 15 | | | | | 20 |
|---|---|---|---|---|---|---|---|---|---|---|---|---|---|---|---|---|---|---|---|---|
| Met | Ile | Arg | Met | Gly | Gly | Arg | Lys | Met | Asn | Pro | Asn | Asn | Arg | Ser | Glu | Tyr | Asp | Thr | Ile |
| ATG | ATA | AGA | ATG | GGA | GGA | AGA | AAA | ATG | AAT | CCA | AAC | AAT | CGA | AGT | GAA | TAT | GAT | ACG | ATA |

| | | | | 25 | | | | | 30 | | | | | 35 | | | | | 40 |
|---|---|---|---|---|---|---|---|---|---|---|---|---|---|---|---|---|---|---|---|
| Lys | Val | Thr | Pro | Asn | Ser | Glu | Leu | Pro | Thr | Asn | His | Asn | Gln | Tyr | Pro | Leu | Ala | Asp | Asn |
| AAG | GTT | ACA | CCT | AAC | AGT | GAA | TTG | CCA | ACT | AAC | CAT | AAT | CAA | TAT | CCT | TTA | GCT | GAC | AAT |

| | | | | 45 | | | | | 50 | | | | | 55 | | | | | 60 |
|---|---|---|---|---|---|---|---|---|---|---|---|---|---|---|---|---|---|---|---|
| Pro | Asn | Ser | Thr | Leu | Glu | Glu | Leu | Asn | Tyr | Lys | Glu | Phe | Leu | Arg | Met | Thr | Ala | Asp | Asn |
| CCA | AAT | TCG | ACA | CTA | GAA | GAA | TTA | AAT | TAT | AAA | GAA | TTT | TTA | AGA | ATG | ACT | GCA | GAC | AAT |

| | | | | 65 | | | | | 70 | | | | | 75 | | | | | 80 |
|---|---|---|---|---|---|---|---|---|---|---|---|---|---|---|---|---|---|---|---|
| Ser | Thr | Glu | Val | Leu | Asp | Ser | Ser | Thr | Val | Lys | Asp | Ala | Val | Gly | Thr | Gly | Ile | Ser | Val |
| TCT | ACG | GAA | GTG | CTA | GAC | AGC | AGC | TCT | ACA | GTA | AAA | GAT | GCA | GTT | ACA | GGG | ATT | TCT | GTT |

| | | | | 85 | | | | | 90 | | | | | 95 | | | | | 100 |
|---|---|---|---|---|---|---|---|---|---|---|---|---|---|---|---|---|---|---|---|
| Val | Gly | Gln | Ile | Leu | Leu | Gly | Val | Val | Gly | Val | Pro | Phe | Ala | Gly | Ala | Leu | Thr | Ser | Phe | Tyr |
| GTA | GGA | CAG | ATT | TTA | TTA | GGT | GTT | GTT | GGG | GTT | CCA | TTT | GCT | GGG | GCG | CTC | ACT | TCA | TTT | TAT |

| | | | | 105 | | | | | 110 | | | | | 115 | | | | | 120 |
|---|---|---|---|---|---|---|---|---|---|---|---|---|---|---|---|---|---|---|---|
| Gln | Ser | Phe | Leu | Asn | Ala | Ile | Trp | Pro | Ser | Asp | Ala | Asp | Pro | Trp | Lys | Ala | Phe | Met | Ala |
| CAA | TCA | TTT | CTT | AAC | GCT | ATA | TGG | CCA | AGT | GAT | GCT | GAC | CCA | TGG | AAG | GCT | TTT | ATG | GCA |

| | | | | 125 | | | | | 130 | | | | | 135 | | | | | 140 |
|---|---|---|---|---|---|---|---|---|---|---|---|---|---|---|---|---|---|---|---|
| Gln | Val | Glu | Val | Leu | Ile | Asp | Lys | Lys | Ile | Glu | Glu | Tyr | Ala | Lys | Ser | Lys | Ala | Leu | Ala |
| CAA | GTG | GAA | GTA | CTG | ATA | GAT | AAG | AAG | ATA | GAG | GAG | TAT | GCT | AAA | AGT | AAA | GCT | CTT | GCA |

| | | | | 145 | | | | | 150 | | | | | 155 | | | | | 160 |
|---|---|---|---|---|---|---|---|---|---|---|---|---|---|---|---|---|---|---|---|
| Glu | Leu | Gln | Gly | Leu | Gln | Asn | Asn | Phe | Glu | Asp | Tyr | Val | Asn | Ala | Leu | Asp | Ser | Trp | Lys |
| GAG | TTA | CAG | GGT | CTT | CAA | AAT | AAT | TTT | GAA | GAT | TAT | GTA | AAT | GCG | TTG | GAT | TCC | TGG | AAG |

FIG.3-2

```
      165                 170                 175                 180
Lys Ala Pro Val Asn Leu Arg Ser Arg Gln Asp Arg Ile Arg Glu Leu Phe Ser
AAA GCG CCT GTA AAT CTT AGA AGT CGA CAA GAT CGA ATA AGA GAA CTT TTT TCT 185                 190                 195                 200
Gln Ala Glu Ser His Phe Arg Asn Ser Met Pro Ser Phe Ala Val Ser Lys Phe Glu Val
CAA GCA GAA AGC CAT TTT CGT AAT TCC ATG CCG TCA TTT GCG GTT TCC AAA TTC GAA GTT 205                 210                 215                 220
Leu Phe Leu Pro Thr Tyr Ala Gln Ala Ala Asn Thr His Leu Leu Lys Asp Ala
CTG TTT CTA CCA ACA TAT GCA CAA GCT GCA AAT ACA CAT TTA CTA AAA GAT GCT 225                 230                 235                 240
Gln Val Phe Gly Glu Trp Gly Tyr Ser Ser Glu Asp Ile Ala Glu Phe Tyr Gln Arg
CAA GTT TTT GGA GAA TGG GGA TAT TCT TCA GAA GAT ATT GCT GAA TTT TAT CAA AGA 245                 250                 255                 260
Gln Leu Lys Leu Thr Gln Gln Tyr Thr Tyr Asp His Cys Val Asn Trp Tyr Asn Val Gly Leu
CAA TTA AAA CTT ACG CAA CAA TAC ACT TAT GAT CAT TGT GTC AAT TGG TAT AAT GTT GGA TTA 265                 270                 275                 280
Asn Ser Leu Arg Gly Ser Thr Tyr Asp Ala Trp Val Lys Phe Asn Arg Phe Arg Arg Glu
AAT AGT TTA AGA GGT TCA ACT TAT GAT GCA TGG GTC AAA TTT AAC CGT TTT CGC AGA GAA 285                 290                 295                 300
Met Thr Leu Thr Val Leu Asp Leu Ile Val Leu Phe Pro Phe Tyr Asp Val Arg Leu Tyr
ATG ACA TTA ACT GTA TTA GAT CTA ATT GTA TTA TTC CCA TTT TAT GAT GTT CGG TTA TAC
```

FIG.3-3

```
     305             310             315             320
Ser Lys Gly Val Lys Thr Glu Leu Thr Arg Asp Ile Phe Thr Asp Pro Ile Phe Thr Leu
TCA AAA GGA GTT AAA ACA GAA CTA ACA AGA GAC ATT TTT ACA GAT CCA ATT TTT ACA CTC 325             330             335             340
Asn Ala Leu Gln Glu Tyr Gly Pro Thr Phe Ser Ser Ile Glu Asn Ser Ile Arg Lys Pro
AAT GCT CTT CAA GAG TAT GGA CCA ACT TTT TCG AGT ATA GAA AAC TCT ATT CGA AAA CCT 345             350             355             360
His Leu Phe Asp Tyr Leu Arg Gly Ile Glu Phe His Thr Arg Leu Arg Pro Gly Tyr Ser
CAT TTA TTT GAT TAT TTG CGT GGG ATT GAA TTT CAT ACG CGT CTT CGA CCT GGT TAC TCT 365             370             375             380
Gly Lys Asp Ser Phe Asn Tyr Trp Ser Gly Asn Tyr Val Glu Thr Arg Pro Ser Ile Gly
GGG AAA GAT TCT TTC AAT TAT TGG TCT GGT AAT TAT GTA GAA ACT AGA CCT AGT ATA GGA 385             390             395             400
Ser Asn Asp Thr Ile Thr Ser Pro Phe Tyr Gly Asp Lys Ser Ile Glu Pro Ile Gln Lys
TCT AAT GAT ACA ATC ACT TCC CCA TTT TAT GGA GAT AAA TCT ATT GAA CCT ATA CAA AAG 405             410             415             420
Leu Ser Phe Asp Gly Gln Lys Val Tyr Arg Thr Ile Ala Asn Thr Asp Ile Ala Ala Phe
CTA AGC TTT GAT GGA CAA AAA GTT TAT CGA ACT ATA GCT AAT ACA GAC ATA GCG GCT TTT 425             430             435             440
Pro Asp Gly Lys Ile Tyr Phe Gly Val Thr Lys Val Asp Phe Ser Gln Tyr Asp Asp Gln
CCG GAT GGC AAG ATA TAT TTT GGT GTT ACG AAA GTT GAT TTT AGT CAA TAT GAT GAT CAA 445             450             455             460
Lys Asn Glu Thr Ser Thr Gln Thr Tyr Asp Ser Lys Arg Tyr Asn Gly Tyr Leu Gly Ala
AAA AAT GAA ACT AGT ACA CAA ACA TAT GAT TCA AAA AGA TAC AAT GGC TAT TTA GGT GCA
```

FIG.3-4

```
            465                 470                 475                 480
Gln Asp Ser Ile Asp Gln Leu Pro Pro Glu Thr Thr Asp Glu Lys Ala Tyr
CAG GAT TCT ATC GAC CAA TTA CCA CCA GAA ACA ACA GAT GAA AAA GCA TAT 485                 490                 495                 500
Ser His Gln Leu Asn Tyr Ala Glu Cys Phe Leu Met Gln Asp Arg Arg Gly Thr Ile Pro
AGT CAT CAG CTT AAT TAC GCA GAA TGT TTC TTA ATG CAG GAC CGT CGT GGA ACA ATT CCA 505                 510                 515                 520
Phe Phe Trp Thr His Arg Ser Val Asp Phe Phe Asn Thr Ile Asp Ala Glu Lys Ile
TTT TTT TGG ACT CAT AGA AGT GTA GAC TTT TTT AAT ACA ATT GAT GCT GAA AAA ATT 525                 530                 535                 540
Thr Gln Leu Pro Val Val Lys Ala Tyr Ala Leu Ser Ser Gly Ala Ser Ile Ile Glu Gly
ACT CAA CTT CCA GTA GTG AAA GCA TAT GCC TTG TCT TCA GGC GCT TCC ATT ATT GAA GGT 545                 550                 555                 560
Pro Gly Phe Thr Gly Gly Asn Leu Leu Phe Leu Lys Glu Ser Ser Asn Ser Ile Ala Lys
CCA GGA TTC ACA GGA GGA AAT TTA CTA TTC CTA AAA GAA TCT AGT AAT TCA ATT GCT AAA 565                 570                 575                 580
Phe Lys Val Thr Leu Asn Ser Ala Ala Leu Leu Gln Arg Tyr Arg Val Arg Ile Arg Tyr
TTT AAA GTT ACC TTA AAT TCA GCA GCC TTG CAA CGA TAT CGC GTA AGA ATA CGC TAT 585                 590                 595                 600
Ala Ser Thr Thr Asn Leu Arg Leu Phe Val Gln Asn Ser Asn Asp Phe Leu Val Ile
GCT TCA ACC ACT AAC CTA CGA CTT TTC GTG CAA AAT TCA AAC GAT TTT CTT GTC ATC 605                 610                 615                 620
Tyr Ile Asn Lys Thr Met Asn Ile Asp Gly Asp Leu Thr Tyr Gln Thr Phe Asp Phe Ala
TAC ATT AAT AAA ACT ATG AAT ATA GAT GGT GAT TTA ACA TAT CAA ACA TTT GAT TTC GCA
```

FIG.3-5

```
       625              630              635              640
Thr Ser Asn Ser Asn Met Gly Phe Ser Gly Asp Thr Asn Asp Phe Ile Ile Gly Ala Glu
ACT AGT AAT TCT AAT ATG GGA TTC TCT GGT GAT ACA AAT GAC TTT ATA ATA GGA GCA GAA 645              650              655
Ser Phe Val Ser Asn Glu Lys Ile Tyr Ile Asp Lys Ile Glu Phe Ile Pro Val Gln
TCT TTC GTT TCT AAT GAA AAA ATC TAT ATA GAT AAG ATA GAA TTT ATC CCA GTA CAA
```

4,996,155

BACILLUS THURINGIENSIS GENE ENCODING A COLEOPTERAN-ACTIVE TOXIN

BACKGROUND OF THE INVENTION

The most widely used microbial pesticides are derived from the bacterium *Bacillus thuringiensis*. This bacterial agent is used to control a wide range of leaf-eating caterpillars, Japanese beetles and mosquitos. *Bacillus thuringiensis* produces a proteinaceous paraspore or crystal which is toxic upon ingestion by a susceptible insect host. For example, *B. thuringiensis* var. *kurstaki* HD-1 produces a crystal called a delta toxin which is toxic to the larvae of a number of lepidopteran insects. The cloning and expression of this *B.t.* crystal protein gene in *Escherichia coli* has been described in the published literature (Schnepf, H. E. and Whitely, H. R. [1981] Proc. Natl. Acad. Sci. U.S.A. 78:2893-2897). U.S. Pat. No. 4,448,885 and U.S. Pat. No. 4,467,036 both disclose the expression of *B.t.* crystal protein in *E. coli*. European Patent Application, Publication No. 0 202 739, discloses a novel *B. thuringiensis* microbe which can be used to control coleopteran pests in various environments.

BRIEF SUMMARY OF THE INVENTION

Disclosed and claimed is a novel toxin gene toxic to coleopteran insects. This toxin gene can be transferred to suitable hosts via plasmid vector.

Specifically, the invention comprises a novel delta endotoxin gene which encodes a 74.228 kd protein which is active against coleopteran pests.

More specifically, the subject invention concerns a novel toxin gene (DNA) encoding a novel protein having activity against coleopteran insects. Table 1 discloses the DNA encoding the novel toxin. Table 2 discloses the amino acid sequence of the novel hybrid toxin. Table 3 is a composite of Tables 1 and 2.

BRIEF DESCRIPTION OF THE DRAWINGS

FIG. 1. Nucleotide sequence of novel toxin-encoding gene. The ORF starts as marked with arrow.

FIG. 2. Deduced amino acid sequence of novel toxin.

FIG. 3. Nucleotide sequence and corresponding amino acid sequence of novel toxin.

DETAILED DISCLOSURE OF THE INVENTION

The novel toxin gene of the subject invention was obtained from a novel coleopteran-active *B. thuringiensis* (*B.t.*) isolate designated 43F. The gene was isolated using the open reading frame (ORF) of the delta endotoxin gene from *B.t.* var. *san diego* (*B.t.s.d.*) as a probe. *B.t.s.d.* is available from the culture repository in Peoria, Ill. U.S.A., identified in detail, infra. where its accession number is NRRL B-15939. The gene was cloned on a 7.5 Kb EcoRI fragment in Lambda ZAP ™ (Stratagene Cloning Systems). This cloning vehicle readily yielded the cloned gene in the plasmid BLUESCRIPT ™ (Stratagene). Sequence and expression data are in agreement with an open reading frame of 1963 bp that encodes a protein of 74.228 Kd.

*B. thuringiensis* isolate 43F, NRRL B-18298, can be cultured using standard known media and fermentation techniques. Upon completion of the fermentation cycle, the bacteria can be harvested by first separating the *B.t.* spores and crystals from the fermentation broth by means well known in the art. The recovered *B.t.* spores and crystals can be formulated into a wettable powder, a liquid concentrate, granules or other formulations by the addition of surfactants, dispersants, inert carriers and other components to facilitate handling and application for particular target pests. The formulation and application procedures are all well known in the art and are used with commercial strains of *B. thuringiensis* (HD-1) active against Lepidoptera, e.g., caterpillars. *B.t.* isolate 43F can be used to control coleopteran pests.

Subcultures of *B.t.* isolate 43F and the *E. coli* host harboring the toxin gene of the invention, *E. coli* XL1-blue (pM1,98-4) were deposited in the permanent collection of the Northern Research Laboratory, U.S. Department of Agriculture, Peoria, Ill., U.S.A. on Feb. 2, 1988, and on Jan.15, 1988, respectively. The accession numbers are as follows:

*B.t.* isolate 43F—NRRL B-18298

*E. coli* XL1-Blue (pM1,98-4)—NRRL B-18291

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

The toxin gene of the subject invention can be introduced into a wide variety of microbial hosts. Expression of the toxin gene results, directly or indirectly, in the intracellular production and maintenance of the pesticide. With suitable hosts, e.g., Pseudomonas, the microbes can be applied to the situs of coleopteran insects where they will proliferate and be ingested by the insects. The result is a control of the unwanted insects. Alternatively, the microbe hosting the toxin gene can be treated under conditions that prolong the activity of the toxin produced in the cell. The treated cell then can be applied to the environment of target pest(s). The resulting product retains the toxicity of the *B.t.* toxin.

Where the *B.t.* toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Methylophilius, Agrobacterium, Acetobacter, Lactobacillus. Arthrobacter, Azotobacter, Leuconostoc, and Alcaligenes; fungi, particularly yeast, e.g., genera Saccharomyces, Cryptococcus, Kluyveromyces, Rhodotorula, and Aureobasidium. Of particular interest are such phytosphere bacterial species as *Pseudomonas syringae. Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii;* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans.* Of particular interest are the pigmented microorganisms.

A wide variety of ways are available for introducing the *B.t.* gene expressing the toxin into the microorganism host under conditions which allow for stable maintenance and expression of the gene. One can provide for DNA constructs which include the transcriptional and translational regulatory signals for expression of the toxin gene, the toxin gene under their regulatory control and a DNA sequence homologous with a sequence in the host organism, whereby integration will occur, and/or a replication system which is functional in the host, whereby integration or stable maintenance will occur.

The transcriptional initiation signals will include a promoter and a transcriptional initiation start site. In some instances, it may be desirable to provide for regulative expression of the toxin, where expression of the toxin will only occur after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a toxin, but upon release into the environment, expression would begin. Other techniques may employ a specific nutrient medium in the laboratory, which inhibits the expression of the toxin, where the nutrient medium in the environment would allow for expression of the toxin. For translational initiation, a ribosomal binding site and an initiation codon will be present.

Various manipulations may be employed for enhancing the expression of the messenger, particularly by using an active promoter, as well as by employing sequences, which enhance the stability of the messenger RNA. The initiation and translational termination region will involve stop codon(s), a terminator region, and optionally, a polyadenylation signal.

In the direction of transcription, namely in the 5′ to 3′ direction of the coding or sense sequence, the construct will involve the transcriptional regulatory region, if any, and the promoter, where the regulatory region may be either 5′ or 3′ of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototropy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene expressing the toxin. In this manner, the enhanced expression of a siderophore may provide for a competitive advantage for the toxin-producing host, so that it may effectively compete with the wild-type microorganisms and stably occupy a niche in the environment.

Where no functional replication system is present, the construct will also include a sequence of at least 50 basepairs (bp), preferably at least about 100 bp, and usually not more than about 1000 bp of a sequence homologous with a sequence in the host. In this way, the probability of legitimate recombination is enhanced, so that the gene will be integrated into the host and stably maintained by the host. Desirably, the toxin gene will be in close proximity to the gene providing for complementation as well as the gene providing for the competitive advantage. Therefore, in the event that a toxin gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the lambda left and right promoters, the Tac promoter, the naturally-occurring promoters associated with the toxin gene, where functional in the host. See for example, U.S. Pat. Nos. 4,332,898, 4,342,832 and 4,356,270. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR322, pACYC184, RSF1010, pRO1614, and the like. See for example, Olson et al., (1982) J. Bacteriol. 150:6069, and Bagdasarian et al., (1981) Gene 16:237, and U.S. Pat. Nos. 4,356,270, 4,362,817, and 4,371,625.

The *B. t.* gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for pesticidal activity.

Suitable host cells, where the pesticide-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Aeromonas, Vibrio, Desulfovibrio, Spirillum; Lactobacillaceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium. Sporobolomyces, and the like.

Characteristics of particular interest in selecting a host cell for purposes of production include ease of introducing the *B.t.i.* gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion,: ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp.; phylloplane organisms such as Pseudomonas sp., Erwinia sp. and Flavobacterium sp.; or such other organisms as Escherichia, Lactobacillus sp., Bacillus sp., and the like. Specific organisms include *Pseudomonas aeruginosa, Pseudomonas fluorescens, Saccharomyces cerevisiae, Bacillus thuringiensis, Escherichia coli, Bacillus subtilis*, and the like.

The cell will usually be intact and be substantially in the proliferative form when treated, rather than in a spore form, although in some instances spores may be employed.

Treatment of the microbial cell, e.g., a microbe containing the *B.t.* toxin gene, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Bouin's fixative and Helly's fixative (See: Humason, Gretchen L., Animal Tissue Techniques, W. H. Freeman and Company, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like.

The cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

The cellular host containing the *B.t.* insecticidal gene may be grown in any convenient nutrient medium, where the DNA construct provides a selective advantage, providing for a selective medium so that substantially all or all of the cells retain the *B.t.* gene. These cells may then be harvested in accordance with conventional ways. Alternatively, the cells can be treated prior to harvesting.

The *B.t.* cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The pesticidal concentration will vary widely depending upon the nature of the particular formulation, particularly whether it is a concentrate or to be used directly. The pesticide will be present in at least 1% by weight and may be 100% by weight. The dry formulations will have from about 1-95% by weight of the pesticide while the liquid formulations will generally be from about 1-60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the coleopteran pest(s), e.g., plants, soil or water, by spraying, dusting, sprinkling, or the like.

Following are examples which illustrate procedures, including the best mode, for practicing the invention. These examples should not be construed as limiting. All percentages are by weight and all solvent mixture proportions are by volume unless otherwise noted. Example 1—Cloning of Novel Toxin Gene and Transformation into *Bacillus megaterium*

Total cellular DNA was prepared by growing the cells of *B.t.* isolate 43F and *B.t.s.d.* to a low optical density ($OD_{600}=1.0$) and recovering the cells by centrifugation. The cells were protoplasted in a buffer containing 20% sucrose and 50 mg/ml lysozyme. The protoplasts were lysed by addition of SDS to a final concentration of 4%. The cellular material was precipitated overnight at 4° C. in 100 mM neutral potassium chloride. The supernate was phenol/chloroform extracted twice and the DNA precipitated in 68% ethanol. The DNA was purified on a cesium chloride gradient. DNA's from strains 43F and *B.t.s.d.* (as a standard of reference) were digested with EcoRI and run out on a 0.8% agarose gel. The gel was Southern blotted and probed with the nick translated ORF XmnI to PstI fragment of the toxin encoding gene isolated from *B.t.s.d.* (this will be subsequently referred to as probe). The results showed 43F to hybridize to probe at 7.5 Kb which is different than the standard.

Preparative amounts of 43F DNA were digested with EcoRI and run out on a 0.8% agarose gel. The 7.5 Kb region of the preparative gel was isolated and the DNA electroeluted and concentrated using an ELU-TIP ™-d (Schleicher and Schuell, Keene, NH) ion exchange column. A sample was blotted and probed to verify the fragment was indeed isolated. The 7.5 Kb EcoRI fragment was ligated to Lambda ZAP ™ EcoRI arms. The packaged recombinant phage were plated out with *E. coli* strain BB4 (Stratagene Cloning Systems, La Jolla, Calif.) to give high plaque density.

The plaques were screened by standard procedures with probe. The plaques that hybridized were purified and rescreened at a lower plaque density. The resulting phage were grown with M13 helper phage (Stratagene) and the recombinant BLUESCRIPT ™ plasmid was automatically excised and packaged. The "phagemid" was re-infected in XL1-blue *E. coli* cells (Stratagene) as part of the automatic excision process. The infected XL1-blue cells were screened for ampicillin resistance and the resulting colonies were miniprepped to find the desired plasmid pM1,98-4. The recombinant *E. coli* XL1-Blue (pM1,98-4) strain is called MR381.

The plasmid pM1,98-4 contained a 7.5 Kb EcoRI insert. To verify that this insert was the one of interest, a Southern blot was performed and probed. The 7.5 Kb band hybridized with the probe, confirming that the fragment had been cloned. Restriction endonuclease analysis of the 7.5 Kb EcoRI fragment with the enzymes HindIII, PstI, SpeI, BamHI and XbaI was done to show that a coleopteran gene different than *B.t.s.d.* had been cloned. The enzymes which cut inside the 7.5 Kb EcoRI fragment were HindIII (twice) SpeI (twice) and PstI (once). The ORF of the 43F gene cuts once with HindIII, twice with SpeI and does not cut with XbaI, EcoRI, or BamHI. In comparison to the coleopteranactive gene already cloned and sequenced, the 7.5 Kb EcoRI fragment shows no similarity in its restriction map. Sequence data shows an open reading frame of 1963 bp with at best 70% homology to the toxin encoding gene of *B.t.sd.* The recombinant BLUESCRIPT ™ plasmid has been fused with the Bacillus plasmid pBC16-1SpeI and transformed into *B. megaterium* for expression by the following procedure. The plasmid pM1,98-4 was completely digested with XbaI. The Bacillus vector pBC16-1, received from the Bacillus Genetic Stock Center (Ohio State University), was terminally digested with EcoRI and then made blunt-ended by filling the 5' overhang using the Klenow fragment and deoxynucleotide triphosphates. SpeI linker was added and the resulting plasmid was called pBC16-1SpeI. This plasmid was terminally digested with SpeI. The XbaI overhang of pM1,98-4 (XbaI linear) and the SpeI overhang of pBC16-1SpeI (SpeI linear) are complementary. The two were fused together with T4 DNA Ligase and transformed into competent *E. coli* cells DH5 (BRL). Screening of tetracyclineresistant colonies produced the desired plasmid called pM2,18-1. This plasmid was then transformed, using standard procedures, into *B. megatarium*. *B. megatarium* (pM2,18-1) was grown to sporulation producing crystal inclusions. Polyacrylamide gel analysis of a spore crystal preparation suggests that an approximately 70 Kd molecular weight protein is being produced. This is in agreement with the molecular mass of 74.228 Kd predicted from the amino acid sequence as deduced from the nucleotide sequence. The novel gene of the invention has homology to the *B.t.s.d.* toxin gene but is clearly distinguished from the *B.t.s.d.* gene by a unique nucleotide sequence.

Data from standard insect tests show that the novel toxin of the invention is active against *Leptinotarsa texana*, a surrogate test species for the Colorado Potato Beetle (CPB). Novel *B.t.* isolate 43F has been shown to be active against *L. texana* and CPB.

The above cloning procedures were conducted using standard procedures unless otherwise noted.

The various methods employed in the preparation of the plasmids and transformation of host organisms are well known in the art. These procedures are all described in Maniatis, T., Fritsch, E. F., and Sambrook, J. (1982) *Molecular Cloning: A Laboratory Manual*, Cold Spring Harbor Laboratory, New York. Thus, it is within the skill of those in the genetic engineering art to extract DNA from microbial cells, perform restriction enzyme digestions, electrophorese DNA fragments, tail and anneal plasmid and insert DNA, ligate DNA, transform cells, prepare plasmid DNA, electrophorese proteins, and sequence DNA.

The restriction enzymes disclosed herein can be purchased from Bethesda Research Laboratories, Gaithersburg, Md., or New England Biolabs, Beverly, Mass. The enzymes are used according to the instructions provided by the supplier.

Plasmid pM1,98-4 containing the *B.t.* toxin gene, can be removed from the transformed host microbe by use of standard well-known procedures. For example, *E. coli* XL1-Blue (pM1,98-4) can be subjected to cleared lysate isopycnic density gradient procedures, and the like, to recover pM1,98-4.

Example 2—Insertion of Toxin Gene Into Plants

The novel gene coding for the novel insecticidal toxin, as disclosed herein, can be inserted into plant cells using the Ti plasmid from *Agrobacter tumefaciens*. Plant cells can then be caused to regenerate into plants (Zambryski, P., Joos, H., Gentello, C., Leemans, J., Van Montague, M. and Schell, J [1983] Cell 32:1033–1043). A particularly useful vector in this regard is pEND-4K (Klee, H. J., Yanofsky, M. F. and Nester, E. W. [1985] Bio/Technology 3:637–642). This plasmid can replicate both in plant cells and in bacteria and has multiple cloning sites for passenger genes. The toxin gene, for example, can be inserted into the BamHI site of pEND4K, propagated in *E. coli*, and transformed into appropriate plant cells.

Example 3—Cloning of Novel *B. thuringiensis* Gene Into Baculoviruses

The novel gene of the invention can be cloned into baculoviruses such as *Autographa californica* nuclear polyhedrosis virus (AcNPV). Plasmids can be constructed that contain the AcNPV genome cloned into a commercial cloning vector such as pUC8. The AcNPV genome is modified so that the coding region of the polyhedrin gene is removed and a unique cloning site for a passenger gene is placed directly behind the polyhedrin promoter. Examples of such vectors are pGP-B6874, described by Pennock et al. (Pennock, G. D., Shoemaker, C. and Miller, L. K. [1984] Mol. Cell. Biol. 4:399–406), and pAC380, described by Smith et al. (Smith, G. E., Summers, M. D. and Fraser, M. J. [1983] Mol Cell. Biol. 3:2156–2165). The gene coding for the novel protein toxin of the invention can be modified with BamHI linkers at appropriate regions both upstream and downstream from the coding region and inserted into the passenger site of one of the AcNPV vectors.

As disclosed previously, the nucleotide sequence encoding the novel *B.t.* toxin gene is shown in Table 1. The deduced amino acid sequence is shown in Table 2.

It is well known in the art that the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| | | | |
|---|---|---|---|
| Phenylalanine (Phe) | TTK | Histidine (His) | CAK |
| Leucine (Leu) | XTY | Glutamine (Gln) | CAJ |
| Isoleucine (Ile) | ATM | Asparagine (Asn) | AAK |
| Metionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |
| Threonine (Thr) | ACL | Tryptophan (Trp) | TGG |
| Alanine (Ala) | GCL | Arginine (Arg) | WGZ |
| Tyrosine (Tyr) | TAK | Glycine (Gly) | GGL |
| Termination signal | TAJ | | |

Key: Each 3-letter deoxynucleotide triplet corresponds to a trinucleotide of mRNA, having a 5'-end on the left and a 3'-end on the right. All DNA sequences given herein are those of the strand whose sequence correspond to the mRNA sequence, with thymine substituted for uracil. The letters stand for the purine or pyrimidine bases forming the deoxynucleotide sequence.

A = adenine
G = guanine
C = cytosine
T = thymine
X = T or C if Y is A or G
X = C if Y is C or T
Y = A, G, C or T if X is C
Y = A or G if X is T
W = C or A if Z is A or G
W = C if Z is C or T
Z = A, G, C or T if W is C
Z = A or G if W is A
QR = TC if S is A, G, C or T; alternatively QR = AG if S is T or C
J = A or G
K = T or C
L = A, T, C or G
M = A, C or T The above shows that the novel amino acid sequence of the *B.t.* toxin can be prepared by equivalent nucleotide sequences encoding the same amino acid sequence of the protein. Accordingly, the subject invention includes such equivalent nucleotide sequences. In addition it has been shown that proteins of identified structure and function may be constructed by changing the amino acid sequence if such changes do not alter the protein secondary structure (Kaiser, E. T. and Kezdy, F. J. [1984] Science 223:249–255). Thus, the subject invention includes mutants of the amino acid sequence depicted herein which do not alter the protein secondary structure, or if the structure is altered, the biological activity is retained to some degree.

We claim:

1. Essentially pure DNA encoding a *B.t.* toxin having the amino acid sequence shown in FIG. 2.

2. Essentially pure DNA according to claim 1, having the nucleotide sequence shown in FIG. 1.

3. A recombinant DNA transfer vector comprising DNA having all or part of the nucleotide sequence which codes for the amino acid sequence shown in FIG. 2.

4. The DNA transfer vector, according to claim 3, transferred to and replicated in a prokaryotic or eukaryotic host.

5. A bacterial host transformed to express a *B.t.* toxin having the amino acid sequence shown in FIG. 2.

6. *Bacillus megaterium*, according to claim 5, transformed with a plasmid vector containing the *B.t.* toxin gene encoding the *B.t.* toxin having the amino acid sequence shown in FIG. 2.

7. *E. coli* XL1-Blue (pM1,98-4), having the identifying characteristics of NRRL B-18291, a host according to claim 5.

8. A microorganism according to claim 5, which is a species of *Pseudomonas, Azotobacter, Erwinia, Serratia, Klebsiella, Rhizobium, Rhodopseudomonas, Methylophilius, Agrobacterium, Acetobacter* or *Alcaligenes*.

9. A microorganism according to claim 8, wherein said microorganism is pigmented and phylloplane adherent.

10. An insecticidal composition comprising insecticide containing substantially intact, treated cells having prolonged pesticidal activity when applied to the environment of a target pest, wherein said insecticide is a polypeptide toxic to coleopteran insects, is intracellular, and is produced as a result of expression of a transformed microbe capable of expressing the *B.t.* toxin having the amino acid sequence shown in FIG. 2.

11. The insecticidal composition, according to claim 10, wherein said treated cells are treated by chemical or physical means to prolong the insecticidal activity in the environment.

12. The insecticidal composition, according to claim 11, wherein said cells are prokaryotes or lower eukaryotes.

13. The insecticidal composition, according to claim 12, wherein said prokaryotic cells are selected from the group consisting of Enterobacteriaceae, Bacillaceae, Rhizobiaceae, Spirillaceae, Lactobacillaceae, Pseudomonadaceae, Azotobacteraceae, and Nitrobacteraceae.

14. The insecticidal composition, according to claim 12, wherein said lower eukaryotic cells are selected from the group consisting of Phycomycetes, Ascomycetes, and Basidiomycetes.

15. The insecticidal composition, according to claim 10, wherein said cell is a pigmented bacterium, yeast, or fungus.

16. Treated, substantially intact unicellular microorganism cells containing an intracellular toxin, which toxin is a result of expression of a *Bacillus thuringiensis* toxin gene toxic to coleopteran insects which codes for a polypeptide toxin having the amino acid sequence shown in FIG. 2, wherein said cells are treated under conditions which prolong the insecticidal activity when said cell is applied to the environment of a target insect.

17. The cells, according to claim 16, wherein the cells are treated by chemical or physical means to prolong the insecticidal activity in the environment.

18. The cells according to claim 16, wherein said microorganism is Pseudomonas and said toxin is a *B.t.* toxin having the amino acid sequence shown in FIG. 2.

19. Pseudomonas cells according to claim 18, wherein said cells are treated with iodine.

20. The cells, according to claim 16, which are *Pseudomonas fluorescens*.

21. Plasmid denoted pM1,98-4.

22. *B. megatarium* (pM2,18-1), according to claim 6.

23. Plasmid denoted pM2,18-1.

* * * * *

UNITED STATES PATENT AND TRADEMARK OFFICE
CERTIFICATE OF CORRECTION

PATENT NO. : 4,996,155

DATED : February 26, 1991

INVENTOR(S) : Sick et al

It is certified that error appears in the above-identified patent and that said Letters Patent is hereby corrected as shown below:

| | | |
|---|---|---|
| Column 2: | line 51: | "Pseudomonas" should read --Pseudomonas--. |
| Column 3: | line 13: | After "Rhizobium" insert --Rhodopseudomonas--. |
| Column 3: | line 17: | After "Kluyveromyces" insert --Sporobolomyces--. |
| Column 5: | line 50: | After "Zymomonas" insert --Serratia--. |
| Column 7: | line 13: | After "The" delete extra spaces. |
| Column 8: | line 25: | After "otherwise noted." start new paragraph. |
| Column 8: | line 37: | "tetracyclineresistant" should read --tetracycline resistant--. |

Signed and Sealed this

Eleventh Day of August, 1992

Attest:

DOUGLAS B. COMER

Attesting Officer

Acting Commissioner of Patents and Trademarks